United States Patent [19]

Larson et al.

[11] Patent Number: 4,692,535

[45] Date of Patent: Sep. 8, 1987

[54] PURIFICATION OF PROPYLENE OXIDE

[75] Inventors: Harold V. Larson, Houston, Tex.; Hyman D. Gillman, Spring City, Pa.

[73] Assignee: Atlantic Richfield Company, Los Angeles, Calif.

[21] Appl. No.: 944,896

[22] Filed: Dec. 22, 1986

[51] Int. Cl.$^4$ ............................................ C07D 301/32
[52] U.S. Cl. .................................................. 549/542
[58] Field of Search ....................................... 549/542

[56] References Cited

U.S. PATENT DOCUMENTS 4,233,202 11/1980 Berger et al. ....................... 549/542

Primary Examiner—Norma S. Milestone
Attorney, Agent, or Firm—Michael S. Jarosz

[57] ABSTRACT

Process for improving the quality of propylene oxide contaminated with minute quantities of high molecular weight poly(propylene oxide) by contacting liquid propylene oxide with certain solid adsorbents, such as activated carbon and attapulgite, thereby obtaining a substantially pure oxide product essentially free of high molecular weight poly(propylene oxide) suitable for conversion of polyether polyols capable of producing high resilient flexible polyurethane foams exhibiting high rise and substantially free of blow hole formation.

8 Claims, No Drawings

PURIFICATION OF PROPYLENE OXIDE

BACKGROUND OF THE INVENTION

1. Field of the Invention

This invention relates to a method of purifying propylene oxide. More particularly, this invention is concerned with the production of quality propylene oxide product which is capable of being commercially employed as an intermediate for the production of polyether polyols which are employed in the preparation of high resilient flexible polyurethane foams which exhibit high rise and are substantially free of blow hole formation.

Propylene oxide is a valuable precursor for the preparation of polyether polyols which are employable in the production of flexible polyurethane foams by reaction with a polyisocyanate in the presence of a blowing agent. In general, commercially available propylene oxide for this purpose is of high purity, substantially all impurities having been removed prior to commercial availability by subjecting the propylene oxide product to various purification techniques involving distillation and/or separation from other components produced in its preparatory reaction or introduced in purification of the propylene oxide product itself.

2. Description of the Prior Art

Techniques disclosed in the prior art involving purification and/or separation of propylene oxide are extensive. Hence, Jubin U.S. Pat. No. 3,464,897 discloses distillation of propylene oxide admixed with hydrocarbon contaminants in the presence of an open chain or cyclic paraffin containing of from 8 to 12 carbon atoms. Schmidt et al, U.S. Pat. No. 3,843,488 discloses the purification of propylene oxide by fractionation in the presence of a hydrocarbon having of from 8 to 20 carbon atoms. Biola et al Ger Offen. DE No. 2,505,664 discloses the separation of propylene oxide from a reaction mixture in the oxidation of propylene with oxidants. Washall U.S. Pat. No. 3,578,568 discloses the purification of monoepoxides by extractive distillation with ethylene glycol or certain ethers thereof. Ger Offen. DE No. 2,810,662 dated Sept. 13, 1979, discloses the purification of epoxides in a countercurrent extractive distillation process by introduction of an amine-containing compound. Schmidt U.S. Pat. No. 3,881,996 discloses a process for the recovery of propylene oxide in a high state of purity by a series of distillation steps to remove certain aldehydes and other high boiling materials Jubin, U.S. Pat. No. 3,607,669 discloses a method of separating propylene oxide from water by distilling the mixture in the presence of an open chain or cyclic paraffin containing of from 8 to 12 carbon atoms. Although a number of the aforementioned purification or separation techniques, employed alone or in combination, have been successful in the production of commercially acceptable propylene oxide products, it was noted that certain high resilient flexible polyurethane foams based on polyether polyols derived from such commercially available propylene oxide composition would sometimes collapse even though the raw materials employed in the production of such polyurethane foam product, including intermediates therefor, would meet acceptable specifications. Further investigation led to the conclusion that the foam collapse was attributable to the presence of certain nonvolatile impurities present in the propylene oxide starting material employed in the preparation of the polyether polyol. Hence, even after the obtainment of a desired propylene oxide product meeting commercially acceptable specifications, for example by subjecting the crude propylene oxide product to a series of separation and purification techniques, as aforementioned, the ultimate commercial acceptability of the propylene oxide product in the preparation of high resilient flexible foams polyurethane via polyether polyol was unpredictable due to the presence of certain unidentifiable nonvolatile impurities which led to low foam rise and substantial blow hole formation.

SUMMARY OF THE INVENTION

Accordingly, the primary object of the present invention is to provide a method for removing certain nonvolatile contaminants from propylene oxide.

Another object of the present invention is to provide a practical method for obtaining extremely pure propylene oxide compositions.

It is a further object to provide an improved process for the production of stable polyurethane flexible resilient foams.

It has been noted that presently commercially available propylene oxide product, although meeting acceptable chemical specifications, does not always produce acceptable high resilient polyurethane foam due to the presence of blow holes and/or low foam rise, although conventional analysis of such foam products has failed to reveal the presence of contaminants which would predict the poor quality of the resultant foam products In accordance with the present invention, it has been found that certain non-volatile impurities, present as poly(propylene oxide) of a molecular weight of at least 50,000, may be removed from crude or commercial grades of propylene oxide by contacting the contaminated propylene oxide with certain solid adsorbents. The purified propylene oxide product, obtained in accordance with the process of the invention, is suitable for conversion to polyether polyols which, upon reaction with a polyisocyanate, yield a high resilient flexible stable polyurethane foam which exhibit high rise and are substantially free of blow hole formation. The method of the present invention, in general, reduces the high molecular poly(propylene oxide) content present in an amount of 0 1 and greater parts per million, to concentrations below 0.1 parts per million, and preferably below about 0.05 parts per million, based on the weight of the propylene oxide product.

DETAILED DESCRIPTION OF THE INVENTION

The process of the present invention, readily adaptable to commercial industrial operation, involves removal of poly(propylene oxide) of high molecular weight generally of at least 50,000, from crude propylene oxide of 95 percent (or above) propylene oxide content, or from propylene oxide of 99+percent purity meeting present commercially acceptable standards, to produce a propylene oxide product of 99.9 to about 100 percent purity and substantially free of high molecular weight poly(propylene oxide) contaminant. The purified propylene oxide resulting from the process of the invention is suitable for direct conversion to highly pure polyether polyols, which, upon reaction with a polyisocyanate in the presence of a blowing agent, provide flexible, stable polyurethane resilient foams exhibiting high rise and are substantially free of blow-hole formation.

The propylene oxide starting material of the purification process of the present invention may be obtained by any of the commercially available routes presently practiced for the production of propylene oxide. Hence, the propylene oxide may be obtained by the classic chlorohydrin route involving reaction of chlorine, propylene and water to form propylene chlorohydrin which is then dehydrochlorinated with calcium hydroxide to form propylene oxide, or alternatively, may be obtained by reaction of propylene with an organic hydroperoxide in the presence of a specified metal catalyst, as disclosed in Kollar U.S. Pat. No. 3,351,635, the disclosure of which is hereby incorporated by reference. The propylene oxide obtained by either of the aforementioned commercial methods may be directly subjected to the process of the present invention, or alternatively, may be first subjected to conventional purification and recovery techniques involving the removal of unreacted reactants, by-products and other treating agents to thereby produce what has been heretofore referred to as propylene oxide meeting acceptable commercial specifications. In accordance with these methods, the propylene oxide is first distilled in the presence of a paraffin to effect separation of propylene oxide from water, removing the major portion of propylene oxide and paraffin bottoms, and followed by removal of the major portion of the water as overhead, in accordance with the processes described in the aforementioned U.S. Pat. Nos. 3,464,897; 3,843,488; 3,881,996; and 3,607,669, the disclosures of which are hereby incorporated herein by reference, prior to subjecting the propylene oxide to the adsorbent treatment in accordance with the process of the present invention.

In accordance with the present invention, it has been found that propylene oxide resulting from any of the aforedescribed methods, may be inherently contaminated with, or may thereafter, during transport or upon storage, for example, upon contact with a metal e.g. carbon steel, become contaminated with a poly(propylene oxide) having a molecular weight of at least about 50,000, and generally greater than about 100,000 conforming to the structural formula

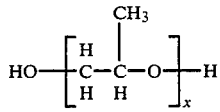

wherein x is an integer of at least about 900, generally, at least 10,000 as determined by gel permeation chromatography, and that this contaminant interferes with the production of stable high resilient polyurethane foam based on polyether polyols derived from such poly(propylene oxide) contaminated compositions. In addition, minute quantities, i.e. generally present in a concentration of less than about 100 p.p.m., of a polyvalent metal-containing contaminant, generally present as an oxide or an alkoxide, for example, oxides or alkoxides of iron, aluminum, chromium, tin, lead, titanium, cobalt, nickel, copper and vanadium, may be substantially completely removed by the adsorbent process of the invention, if present.

Pursuant to the present invention, it has been discovered that propylene oxide contaminated with the aforedescribed poly(propylene oxide) contaminant may be purified by passing propylene oxide liquid through a bed of activated carbon, charcoal, or attapulgite, thereby, removing or reducing the poly(propylene oxide) contaminant content to levels sufficient to permit production of polyether polyols which are suitable, upon reaction with a polyisocyanate in the presence of of blowing agent, to provide high resilient flexible stable polyurethane resilient foams characterized as being substantially free of blow-hole formation and of desired high rise. The treatment with the adsorbent may be effected at temperatures in the range of from about 10° C. to about 100° C. In general, the purification process of the present invention is effected in conventional manner by employing the static-bed percolation process, which is a cyclic process wherein the propylene oxide to be refined is passed through a stationary bed of granular adsorbent under controlled conditions. Propylene oxide subjection to the purification process is continued until the product propylene oxide has attained the desired specification with respect to poly(propylene oxide) contaminant content. Although the treatment with the adsorbent may be effected at a wide range of temperatures, as indicated, treatment with the solid adsorbent may be readily accomplished at temperatures up to about 34° C. at atmospheric pressure. Higher temperatures may be employed in systems employing superatmospheric pressure in both prior recovery or purification systems as well as the solid adsorbent treatment. The use of atmospheric or superatmospheric pressure operations in carrying out the process of this invention is a matter of choice depending upon the relative economics, taking into account the apparatus design and cost. Moreover, the pressure at which the process is carried out has no effect on the concept of the present purification process. Preferred temperatures of treatment reside between about 10° C. and about 35° C. Desirably the pressure is atmospheric, but in the closed system, the pressure employed is slightly above atmospheric i.e. up to about 25 psig.

In general, solid adsorbents, for example, activated carbon, when employed to decolorize solutions, are simply slurried with the solution and then removed as, for example, by filtration. Such adsorbents have also been employed by percolating the solution to be decolorized throughout a bed of the solid adsorbent. For such general decolorizing uses, either method of contacting the solution with the adsorbent has been deemed as equivalent, since substantially the same results are said to be obtained. However, in the method of the present invention, the method of contacting the propylene oxide liquid with the solid adsorbent is important, for more than decolorizing is accomplished. Hence, in the purification of propylene oxide of high purity by the method of this invention, contacting of the propylene oxide with a bed of solid adsorbent, for example activated carbon, results in selective adsorbtion of a heretofore undetected impurity in the form of the aforecharacterized high molecular weight poly(propylene oxide).

The quantity of solid adsorbent employed per unit volume of propylene oxide to be treated will vary not only with the efficiency of the solid adsorbent to absorb impurities, but also with the amount of impurities present at the time of contact. In general, the adsorptive capacity life of the solid adsorbent is limited by the adsorptive capacity for the poly(propylene oxide) contaminant, and not any impurities, e.g. color bodies, that may be present in the propylene oxide liquid itself. For example, with a commercially pure propylene oxide of 99.99 percent impurity, it has been found that from about 0.001 to about 0.01 grams or more of solid adsorbent per gram of propylene oxide being treated will give satisfactory results. Contact time in the range of from about 1 to about 15 minutes will provide sufficient solid adsorbent treatment to attain the objectives of the method of this invention.

As indicated above, not all solid adsorbents are suitable for use in the practice of the purification process of the present invention. Exceptionally useful activated carbons or charcoals include those obtained from lignite, gas black, coconut, bagasse, wood, sawdust, pete, pulp-mill waste, blood, bone, etc. Specific activated carbons include Calgon Corporation granular carbons, NORIT granular activated carbons, Cenco activated carbons, products of Central Scientific Company, Nuchar activated carbons, products of West Virginia Pulp and Paper Company, and products of Darco Division, ICI AMERICAS, Inc. Illustrative commercially available carbons include Type CAL granular carbon (Calgon Corporation) and NORIT RO.8 granular activated carbon (NORIT Corporation). Attapulgite adsorbents employable in the purification process of the present invention are available from Engelhard Minerals and Chemicals Corporation. The grades of Attapulgus Clay normally recommended for contact purification are 100/UP Mesh RVM and 200/UP Mesh RVM. The finer grade 200/UP RVM is normally used unless higher rates of filtration are required, in which case 100/UP RVM is used. In the case of purification by percolation, an adsorbent bed usually consisting of 30/60 Mesh AA LVM Attapulgus Clay is perferred and the liquid allowed to flow downward at controlled temperature and contact time. It is preferred to use the solid adsorbent, i.e. activated carbon, charcoal or attapulgite, in a granular form rather than a powdered form.

Adsorption of the high molecular weight poly (propylene oxide) impurity from liquid propylene oxide has been found to be determined, in conventional manner, by the type of concentration profile in the adsorbent bed column (feed rate and impurity concentration of feed being constant) at any interval of time. This concentration profile is a planar front and therefore the adsorption is chromatographic in nature. Hence, the solution upstream of the planar front contains the feed concentration of the poly(propylene oxide) impurity and the propylene oxide liquid downstream of the planar front contains no poly (propylene oxide) impurity. From this established fact of planar front adsorption, the theoretical performance of a column of various adsorbents, such as activated carbons, can readily be determined from adsorbtion isotherm determinations. It is appreciated that the adsorptive characterists of an adsorbent varies from type of adsorbent to type of adsorbent. Even particle size contributes to the variances. But, by the well known absorption isotherm determination coupled with the established planar front adsorption of poly(propylene oxide) purity, only simple routine tests are required to determine the performance of the column of any specific adsorbent. It is clear from the foregoing that a precise ratio or range of adsorbent to poly(propylene oxide) impurity or crude propylene oxide can not be given since to do so would require testing all known adsorbents which are subject to change by their manufacturer.

To further illustrate the present invention and the manner in which it may be practiced, the following specific examples are set forth. In the examples, unless otherwise indicated, all parts and percentages are by weight.

The adverse effects of high molecular weight poly(propylene oxide) polymer contaminant present in propylene oxide were observed in the synthesis of sensitive polyurethane foams. The following examples illustrate the preparation of the foams and the effect of the presence of the polymer contaminant.

EXAMPLE A

An initiator is prepared first by reacting 473.6 grams of glycerine (5.14 mole) neutralized with 68.2 grams of 87.1% potassium hydroxide (1.059 mole) in a pressure autoclave and removing the water under vacuum. The resultant admixture is then reacted with 1,327 grams of propylene oxide (22.9 mole) to yield a 350 number average molecular weight triol initiator containing 2.2% potassium. This initiator is then reacted with the propylene oxide containing various levels of high molecular weight poly (propylene oxide) as indicated below. To 210 grams of initiator, there is added 2958 grams of propylene oxide (51 moles) and 502 grams of ethylene oxide (11.4 moles) over a ten hour period with stirring at a temperature of between 90° C. and 120° C. The reaction mixture is then heated at 100° C. with stirring for an additional three hours. Thereafter, the reaction mixture is subjected to a vacuum for 1½ hours to remove any unreacted propylene and ethylene oxides and low molecular weight glycols which may have formed. Finally, the resultant product is treated with 80 grams of Maguesal ™ magnesium silicate to remove the potassium by slurrying at 95° C. for two hours and then filtering.

EXAMPLES 1-5

Polyurethane foam formulations are prepared employing the following ingredients:

| Ingredient | Amount (parts, by weight) |
| --- | --- |
| Polyether polyol | 200 |
| Distilled water | 6 |
| Dabco ® WT amine catalyst | 1.4 |
| SH 207M silicone surfactant | 0.6 |
| 80/20 mixture of toluene diisocyanates | 75.2 |
| Crude MDI (PAPI ® 27) | 18.8 |

Various samples of the polyether polyol are prepared using the procedure of Example A, which procedure differs only in the particular propylene oxide used.

All of the ingredients are conditioned at 22°±0.5° C. before producing the foam. The isocyanates are admixed prior to this conditioning. The remainder of the other ingredients which included the polyol, amine catalyst, silicone and water, are mixed after conditioning with high speed stirring for 30 seconds and then degassing for 15 seconds and mixing for another 15 seconds.

The isocyanate admixture is then poured into the polyol mix with stirring at 3000 rpm for 4 seconds. After mixing, 160 parts of this mix is then poured into a one gallon paper bucket, thereby filling the bucket with foam. The quality of the resulting foams is altered by the source of propylene oxide; the results thereof are set forth in Table I, below.

TABLE I

| Example | Propylene Oxide Source Used to Manufacture Polyether Polyol | Appearance of Foam |
|---------|---------|---------|
| 1 | Propylene Oxide containing no detectable amount of high molecular weight poly(propylene oxide) | High resilient foam with uniform cells no blow-holes or shrinkage. |
| 2 | Distilled Propylene Oxide containing 2 ppm of high molecular weight poly(propylene oxide)[(1)] | Foam collapsed to bottom of the bucket. |
| 3 | Distilled Propylene Oxide containing 0.3 ppm of high molecular weight poly(propylene oxide)[(1)] | Foam collapsed to just one inch below the maximum height achieved during blowing numerous Blow-holes appeared on surface of foam. |
| 4 | Distilled Propylene Oxide heated at 82° C. in a carbon steel container for 2 days. | Foam collapsed to several inches below the maximum height achieved during blowing. Numerous large blow-holes appeared on foam surface. |
| 5 | Distilled Propylene Oxide heated at 82° C. in a carbon steel container for 7 days. | Foam collapsed to bottom of the bucket. |

[(1)]High molecular weight poly(propylene oxide) is prepared by heating at 50° C. propylene oxide containing 0.5% zinc hexacyanocobaltate (ZnCo(CN)$_6$) catalyst in tetrahydrofuran (THF); the resulting polymer is characterized by NMR and GPC in conventional manner. The catalyst is then removed by treating the solution with 0.02 parts of magnesium silicate per part of propylene oxide at 120° C. for a period of 2 hours and evaporation of the THF. The polymer is characterized to be poly(propylene oxide) having a molecular weight average of about 500,000.

These examples show that high molecular weight poly(propylene oxide) causes blow holes and collapse in foams (examples 2 and 3) and that high molecular weight poly (propylene oxide) forms upon exposure of propylene oxide to carbon steel (examples 4 and 5).

EXAMPLE 6

A sample of propylene oxide was heated to 82° C. for 20 days in a carbon steel tube. The tube was then allowed to reach room temperature and the propylene oxide was removed. The propylene oxide was then evaporated to dryness and the residue was then taken up in THF. This THF solution was then injected into a preparative GPC and fractions of various molecular weight were isolated. Only those fractions with molecular weight above 50,000 caused adverse effects in the foam formulation described in Examples 1-5, above.

EXAMPLE 7

A solution of propylene oxide containing 10 ppm of synthetic high molecular weight poly(propylene oxide) was passed through a one inch percolation column containing 100 grams of 8×20 lignite carbon (American Norit). The flow rate was 2 bed volume per hour. Samples of the aforedissolved polyether polyol were prepared from this propylene oxide prior to and subsequent to treatment with the carbon. The sample which was untreated caused a complete collapse of the foam in the experiment as described in Examples 1-5. On the other hand, when the polyether polyol produced from the carbon treated propylene oxide sample was used, the resulting foam exhibited high rise and was free of blow holes.

EXAMPLE 8

Experiment 7 was repeated using Calgon CAL 12×40 lignite carbon. The thereby treated propylene oxide sample produced polyether polyol which yielded a totally acceptable foam, whereas the untreated sample caused complete collapse of the foam.

EXAMPLE 9

Experiment 7 was repeated until greater than 10,000 grams of the contaminated propylene oxide had passed through the carbon. The polyether polyol produced from the final portions of this treated propylene oxide caused blow-holes and some slight collapse of the foam. This indicates that break through of the polymer was occurring by this time.

EXAMPLE 10

A sample of propylene oxide containing 1 ppm of synthetic high molecular weight poly(propylene oxide) was passed through a 1″ diameter column containing 100 grams of 16×30 attapulgus clay available from Engelhard Minerals and Chemicals Corporation at a rate of 1-2 bed volumes per hour. The polyether polyol produced from untreated propylene oxide before treatment with the clay caused a large collapse of the foam, whereas a polyether polyol produced from the clay treated propylene oxide yielded a totally acceptable foam of high rise and free of blow holes.

We claim:

1. A method of purifying propylene oxide containing greater than 0.1 p.p.m. of poly(propylene oxide) polymer contaminant of a molecular weight of at least about 50,000 which comprises contacting said propylene oxide at a temperature ranging from between about 10° C. and 100° C. with an adsorbent selected from the group consisting of activated carbon and attapulgite, for a time sufficient to reduce the concentration of said polymer contaminant to below 0.1 p.p.m. and recovering the purified propylene oxide product.

2. The method of claim 1 wherein the contacting with the adsorbent is effected by static bed percolation.

3. The method of claim 2 wherein said adsorbent is activated carbon.

4. The method of claim 2 wherein said adsorbent is attapulgite.

5. The method of claim 2 wherein said adsorbent is granular.

6. The method of claim 2 wherein the propylene oxide starting material additionally is contaminated with an oxide or an alkoxide of at least one polyvalent metal which is substantially removed by contact with the adsorbent.

7. The method of claim 2 wherein the contacting is effected at a temperature of between about 10° C. and 35° C. and the adsorbent is granular activated carbon.

8. The method of claim 7 wherein the polymer contaminant concentration is reduced to below 0.05 p.p.m.

* * * * *